(12) United States Patent
Clark, II (10) Patent No.: US 6,327,920 B1
(45) Date of Patent: Dec. 11, 2001

(54) ON-LINE FLUID SAMPLING DEVICE

(75) Inventor: James E. Clark, II, Ojai, CA (US)

(73) Assignee: C.H. & I Technologies, Inc., Santa Paula, CA (US)

( * ) Notice: Subject to any disclaimer, the term of this patent is extended or adjusted under 35 U.S.C. 154(b) by 0 days.

(21) Appl. No.: 09/117,796

(22) PCT Filed: Feb. 9, 1996

(86) PCT No.: PCT/US96/02145

§ 371 Date: Oct. 26, 1998

§ 102(e) Date: Oct. 26, 1998

(87) PCT Pub. No.: WO97/29353

PCT Pub. Date: Aug. 14, 1997

(51) Int. Cl.[7] .................................................. G01N 1/20
(52) U.S. Cl. ............................................................ 73/864.51
(58) Field of Search ........................... 73/864.51, 863.52, 73/863.81

(56) References Cited

U.S. PATENT DOCUMENTS

| | | | | |
|---|---|---|---|---|
| 3,881,355 | * | 5/1975 | Nelson et al. ..................... | 73/864.51 |
| 4,037,472 | * | 7/1977 | Gates ................................ | 73/864.35 |
| 4,271,704 | * | 6/1981 | Peters .............................. | 73/864.63 |
| 4,548,088 | * | 10/1985 | Hood, Jr. ......................... | 73/864.34 |
| 4,708,011 | * | 11/1987 | Rautakorpi et al. ............. | 73/101.3 X |
| 4,715,789 | * | 12/1987 | Liegel et al. ..................... | 414/253 |
| 4,854,355 | * | 8/1989 | Chazot et al. .................... | 73/863.81 X |
| 5,524,495 | * | 6/1996 | Dudley ............................ | 73/863.52 |
| 5,895,868 | * | 4/1999 | Giammaruti et al. ........... | 73/863.81 |

FOREIGN PATENT DOCUMENTS

| | | | | |
|---|---|---|---|---|
| 2071846 | * | 9/1981 | (GB) ................................ | 73/863.86 |
| 8-43274 | * | 2/1996 | (JP) ................................. | G01N/1/20 |

* cited by examiner

Primary Examiner—Thomas P. Noland
(74) Attorney, Agent, or Firm—Christie, Parker & Hale, LLP (57) ABSTRACT

Fluid sampling device for use in obtaining a precise volume of fluid to be sampled from sealed pressure vessels equipped with a hydraulic fitting to which the fluid sampling devices are connectable. The first embodiment of the device a fluid float chamber with an internally sealable top opening which opens into an upper fluid passage. A floating ball is located in the fluid float chamber and is sized to be sealable at the top opening. A non-floatable ball is sized to seat on a lower seat through which fluid can enter the fluid float chamber. A vacuum line connects between the top opening and the sealed pressure vessel. The second embodiment of the device has a vacuum chamber into which is received a fluid sample container. A fluid supply tube connects between the vacuum chamber and the fluid inlet. A fluid overflow tube also connects between the vacuum chamber and the vacuum cylinder.

5 Claims, 8 Drawing Sheets

ON-LINE FLUID SAMPLING DEVICE

BACKGROUND OF THE INVENTION

1. Field of the Invention

The invention relates to the art of collecting fluid samples, and more particularly to a fluid sampling device for obtaining a sample of a fluid as the fluid is being delivered to a container.

2. State of the Prior Art

Being able to easily take samples of fluids such as motor oil as the fluids are collected from different vehicles and/or machines can be quite useful. In the case of crank case oil in vehicles, particularly trucks, industrial vehicles and machinery, the presence of certain contaminants and the fluid's physical properties can provide vital information about the condition of various parts of the machinery, such as the condition of bearings, pistons, rings etc. Being able to monitor the conditions of these parts can help avoid breakdowns.

U.S. Pat. No. 4,271,704 to Peters discloses a fluid sampler for taking a sample of a fluid in an oil well. A chamber is pressurized with a floating ball so the floating ball seals off the top end of a chamber. The device is lowered into an oil well. When the hydrostatic pressure in the oil well exceeds the pressure in the chamber, oil will fill the chamber, float the floating ball to the top, and again seal off the chamber so that no more oil enters the device. U.S. Pat. No. 4,271,704 to Davidowicz et al. discloses a fluid sampling device with a chamber with two balls—one floating and one non-floating. By pressurizing and depressurizing the float chamber, a precise sample of fluid can be obtained. U.S. Pat. No. 4,715,789 to Liegel et al. discloses a valve assembly for controlling hydraulic fluids. It utilizes balls and springs, but not floating balls.

While these devices may be suitable for obtaining samples from unsealed containers, they are not specifically adapted for taking samples of fluids as the fluids are collected from a particular fluid source, such as from a single vehicle, and delivered to a collection vessel.

BRIEF DESCRIPTION OF THE INVENTION

One object of the invention is to provide an on-line fluid sampling device for use in obtaining a sample of a fluid from a fluid source being delivered to a container, comprising:

a fluid chamber with upper and lower opened ends with a seat located at each end;

a non-floatable ball sized to be seatable on the lower seat and a floatable ball sized to be seatable on the upper seat, said balls thereby being capable of sealing off the seats;

a ball stop positioned in said fluid chamber to prevent said non-floating ball from pushing said floating ball down against said upper seat;

a connector means to detachably place a lower end of said fluid chamber in fluid connection with a fluid line used to deliver fluid to the container; and a vacuum hose adapted to establish a fluid connection between the upper end of said fluid chamber above said upper seat and said container, to place a vacuum on said fluid chamber.

Another object of the computer is to provide an on-line fluid sampling device, for connection to vacuum cylinder into which fluid is suctioned into, said device comprising:

a vacuum chamber which is sized to receive a fluid sample container;

a fluid supply tube in connection between a source of fluid to be sampled and said vacuum chamber;

a fluid overflow tube in connection between said vacuum chamber and the vacuum cylinder.

DETAILED DESCRIPTION OF THE DRAWINGS

DETAILED DESCRIPTION OF THE INVENTION

Figure 1:
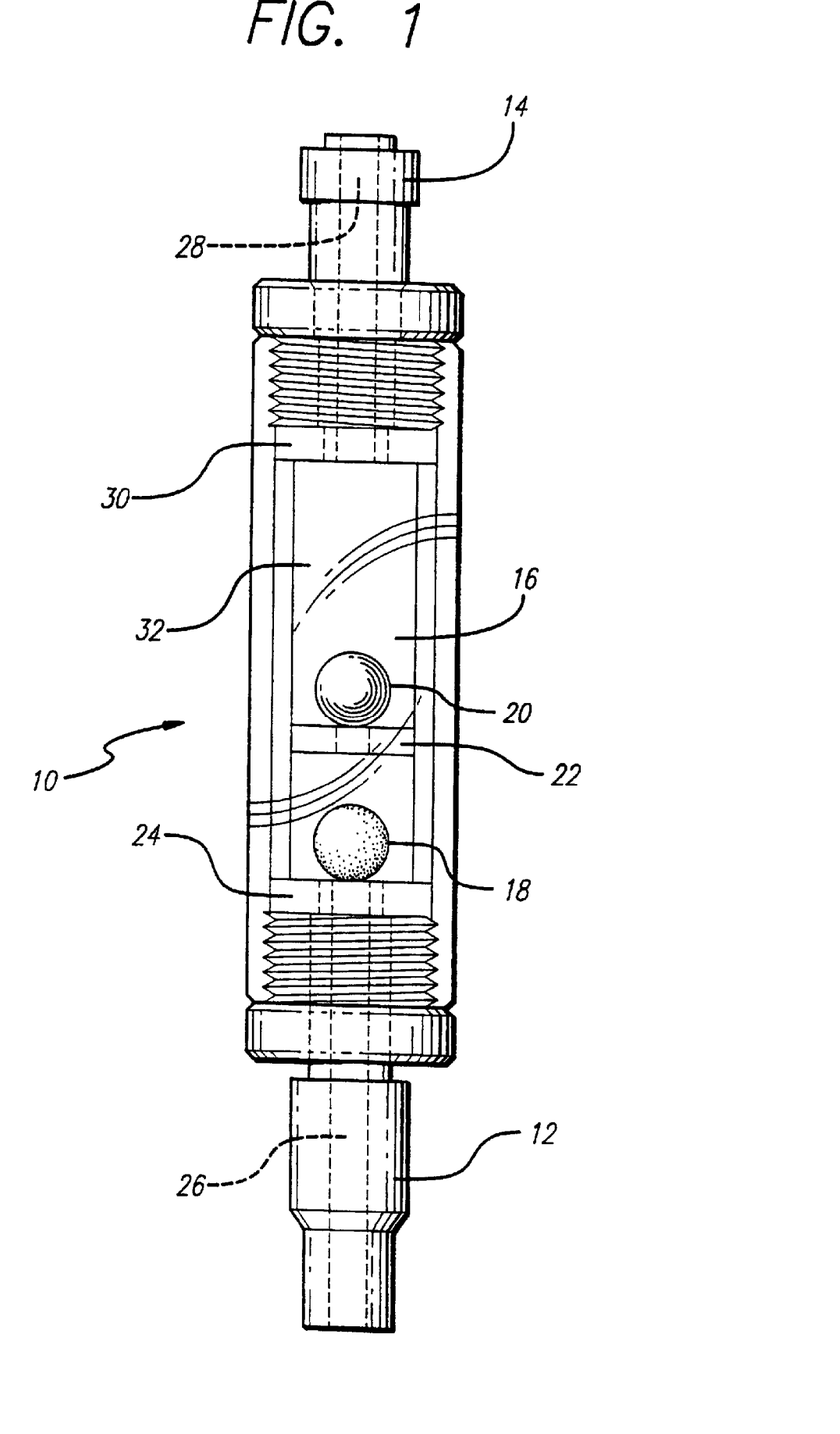
FIG. 1 is a partially exposed side view of a first embodiment of the fluid sampler of the invention, not yet placed on a fluid collection cylinder.

Referring to FIG. 1, a first embodiment of the fluid sampler 10 of the invention is shown. It has a lower attachment end 12 an upper attachment end 14. A fluid chamber 16 is provided in which are retained a non-floating ball 18 (such as a steel ball bearing) and a floating ball 20 (such as provided by a hollow aluminum or plastic ball), separated by a ball stop 22. The fluid chamber 16 has a lower seat 24 upon which the non-floating ball 18 is sized to seatable engage. A lower fluid passage 26 permits fluid communication between the lower attachment end 12 and the fluid chamber 16. The ball stop 22 positioned in the fluid chamber 16 permits fluid to freely pass therethrough, but prevents the two balls 18 and 20 from pushing each other up or down. An upper fluid passage 28 permits fluid communication between an upper seat 30 on the upper attachment end 14. The floating ball 20 is sized to be seatable on the upper seat 30, to block it off. The fluid chamber 16 preferably has a transparent view window 32—so a user can see fluid filling the fluid chamber 16 thereof. This can be easily accomplished by making the fluid chamber from transparent material such as clear plastic or glass.

Figure 2:
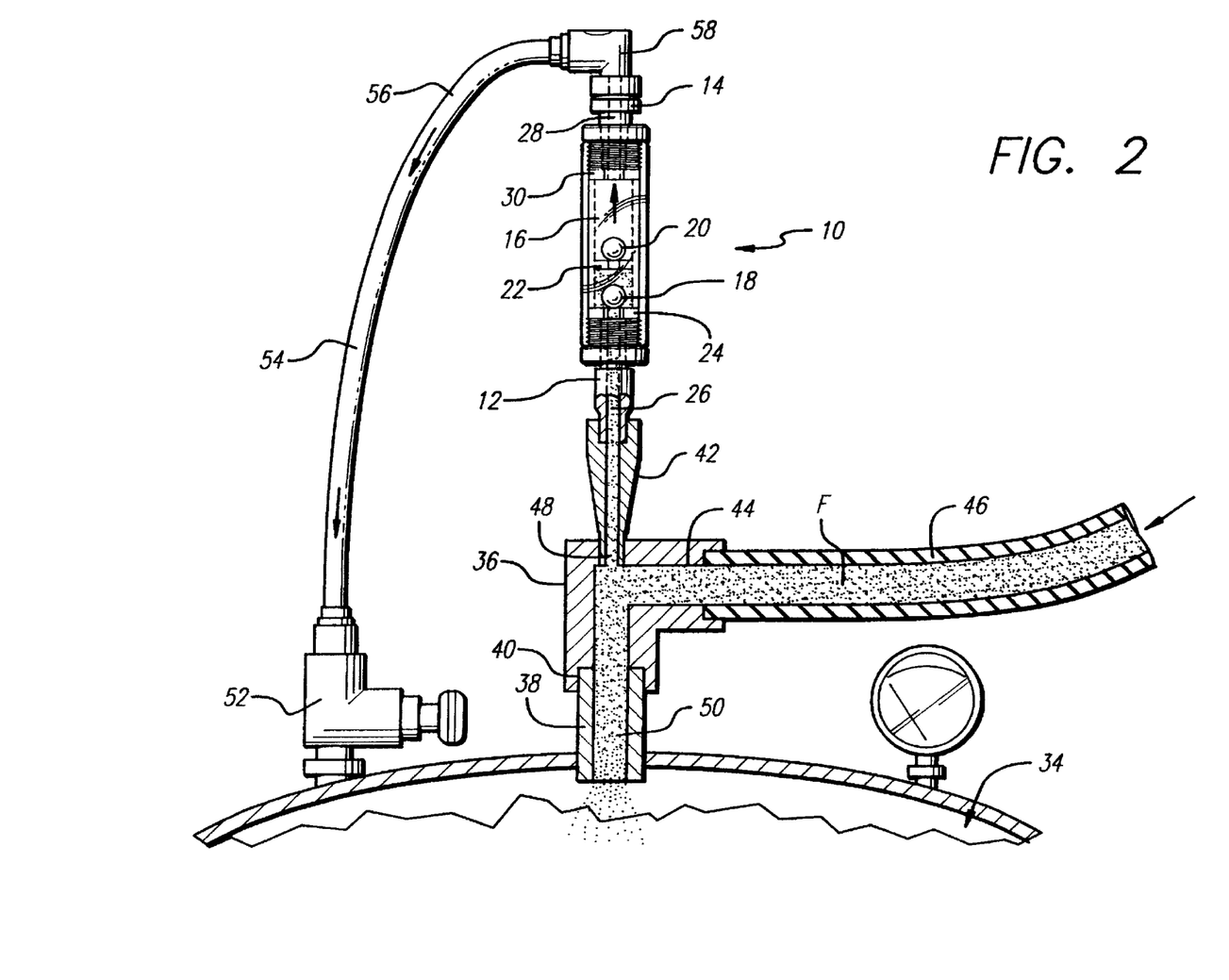
FIG. 2 is a partially exposed view depicting of a fluid sampler of the invention of FIG. 1 attached to a fluid collection cylinder.

Referring now to FIG. 2, the fluid sampler 10 is shown attached to a pressure cylinder 34. The cylinder 34 has a T-fitting 36 attached to an upper fitting 38, preferably with a quick connect hydraulic valve 40. Preferably, the lower attachment end 12 of the device 10 has a quick connect hydraulic valve connector 42. The T-fitting 36 has a fluid inlet 44 connected to a fluid delivery line 46, which is used to collect the fluid to be sampled from the fluid utilizing source, e.g. a motor vehicle's motor crank case. A top port 48 communicates with the fluid inlet 44 and a fluid outlet 50, which thus permits fluid to be delivered to the cylinder 34. A vacuum access port 52 is fitting on the cylinder 34. A vacuum line 54 connects between the vacuum access port 52 and the upper attachment end 14 on the device 10. The upper end 56 of the vacuum line 54 preferably has a quick connect hydraulic fitting 58 for quick connection to the complementary, upper attachment end 14. The optional quick connect hydraulic fittings 58 and 42 permit the device 10 to be quickly and easily disconnected from the cylinder 34 without causing loss of vacuum in the cylinder 34. The cylinder 34 is placed under vacuum and is used to vacuum up fluid, i.e. motor oil, lubricating oil, coolant, and the like, from a machine or vehicle for example, to remove the fluid for replacement with new fluid.

Figure 3:
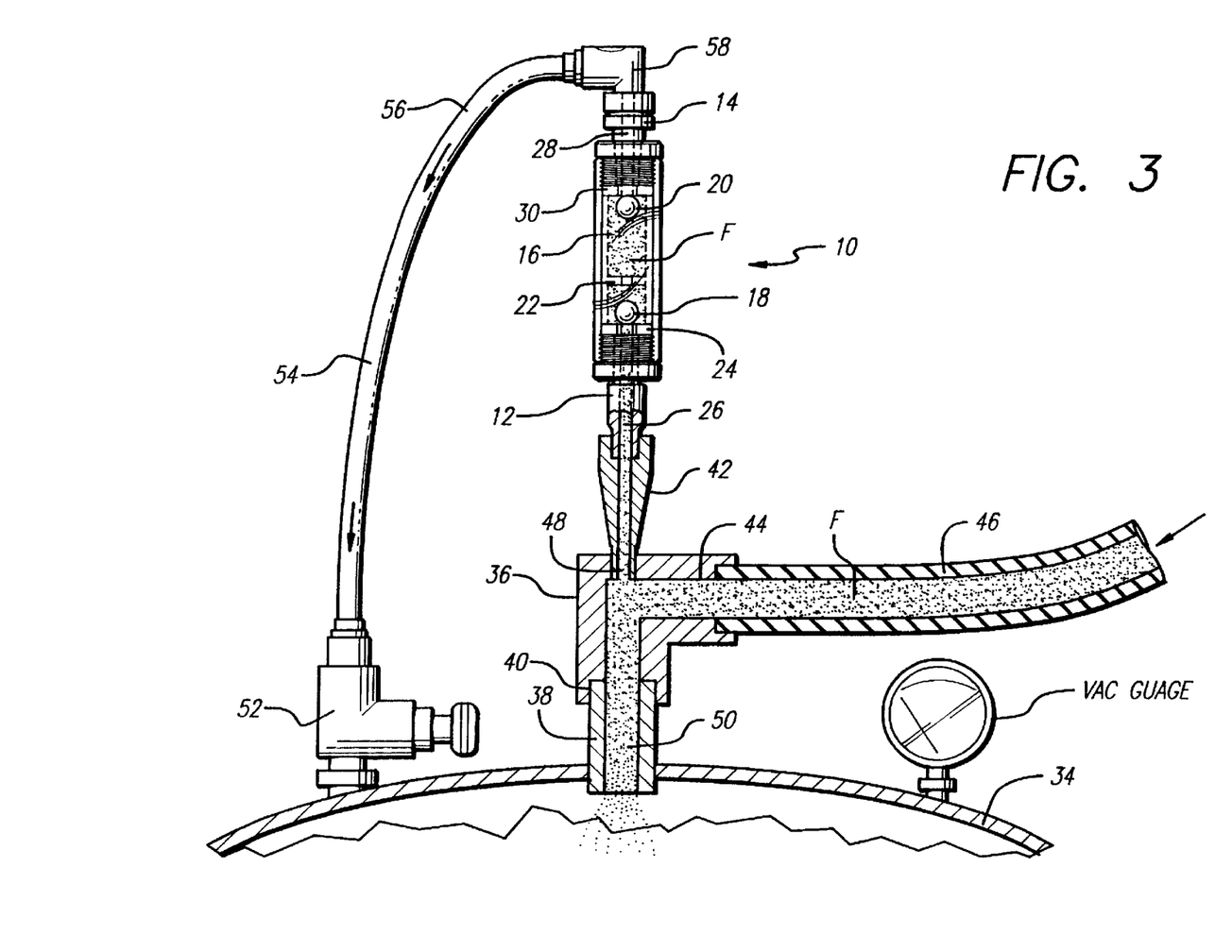
FIG. 3 is a side view of the fluid sampler of FIG. 1 being filled with the sampled fluid.

Referring now to FIGS. 2 and 3, as fluid "F" begins to be vacuum up into the cylinder 34 through the fluid delivery line 46, due to the vacuum be placed on the device's fluid chamber 16 by the vacuum line 54, fluid F will travel through the top port 48 and up the lower fluid passage 26 to fill the fluid chamber 16. The non-floating ball 18 normally seats on the lower set 24. However, due to the presence of the vacuum in the fluid chamber 16, the fluid F will percolate up.

Referring to FIG. 3, as the fluid F continues to fill the fluid chamber 16, the floating ball 20 will float on the fluid F, until it finally floats up and seats on and blocks off the upper seat 30, so no more vacuum is placed on the fluid chamber through the upper fluid channel 28. There being no further vacuum being placed on the fluid chamber 16, the non-floating ball 18 will now seat on the lower seat 24, and prevent any additional fluid F from passing through the lower fluid passage 26.

Figures 4, 5, 6:
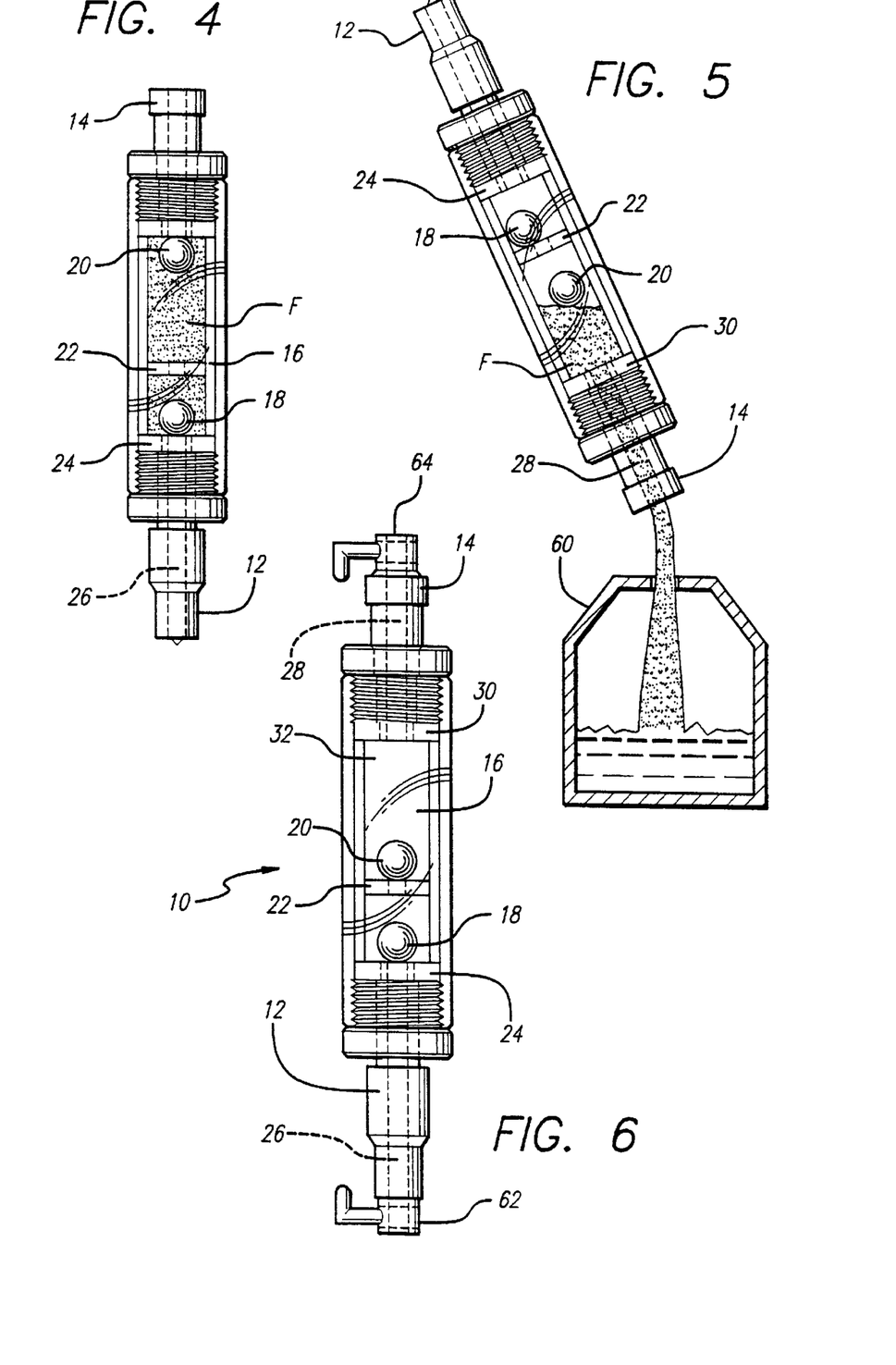
FIG. 4 is a side view of the fluid sampler of FIG. 1 filled with a precise volume of the sampled fluid and removed from the cylinder.
FIG. 5 is a side view of the fluid sampler of FIG. 1 having its collected fluid being emptied into a shipping container.
FIG. 6 is a side view of a second embodiment of the fluids sampler of the invention.

Referring to FIG. 4, the device 10 is detached from the T-fitting 36 and has the vacuum line 56 disconnected therefrom. Due to the presence of the non-floating ball 18 seating on the seat 24, no fluid F will flow out of the lower fluid passage 26. Referring to FIG. 5, the device is then flipped so that its upper tip 14 is pointed down. The rotatable ball 20 will float up away from contact with the upper seat 30, unblocking the upper passage 28, and permitting fluid to be poured into a container 60. In the position, non-floating ball 18 will fall into contact with the ball stop 22, rather than force the floating ball 20 down. The container 60 can comprises a convenient shipping container which can be mailed to an analysis laboratory, so that the collected fluid can be analyzed for impurities and contaminants.

Depending on the relative levels of various contaminants in the sample of fluid, the lab can make an evaluation of the condition of the machine and/or motor. For-example, the presence of coolant in motor oil would indicate coolant leakage. As bearings start to wear, certain types of elements and additives will start to appear in the motor oil. All of these can be measured.

Referring to FIG. 6, the device 10 can be fitted with optional valves 62 and 64 to control fluid flow through the lower and upper passages 26 and 28, respectively, so that the fluid flow into and out of the fluid chamber 16 can be carefully regulated.

Referring to FIGS. 7–10, a third embodiment of an on-line fluid sampling device 70 is shown. It comprises a vacuum chamber 72 in which fits a fluid sample container 74. The vacuum chamber 72 has two parts 76 and 78 which are sealably fittable together, FIGS. 7–10 show a kamlock fitting 80 used to lock the two parts 76 and 78 together, with an airtight seal 82 therebetween. A fluid inlet tube 84 extends through the top 86 of the first part 76 of the vacuum chamber 72, and terminates at an open end 88 in the vacuum chamber 72. A fluid outlet tube 90 also extends through the top 86 of the first part 76 of the vacuum chamber 72, and terminates at an open end 92. The open end 92 of the fluid outlet tube 90 is preferably spaced in the fluid chamber 72 lower than the open end 88 of the fluid inlet tube 84.

A waste fluid vacuum cylinder 94 is fitted with an inlet fitting 96. The inlet fitting 96 has a T-fitting 98 attached thereto. Fluid is drawn in the cylinder 94 through a waste fluid supply tube 100 connected to an inlet end 102 of the T-fitting 98. A quick connect hydraulic fitting 104 is preferably fitted to an outlet end 106 of the T-fitting 98 to allow for quick connection to the waste fluid cylinder's fitting 96. A top port 108 communicates with the T-fitting's fluid passageway 110. The waste fluid vacuum cylinder 94 can be fitted with a vacuum gauge 112 so the user will know at a glance the pressure in the cylinder 94. The cylinder 94 is also fitting with a vacuum inlet 114, with an upper end 116. A sample fluid supply tube 118 connects between the top port 108 of the T-fitting 98 and the fluid inlet tube 84 of the vacuum chamber 72. A sample fluid overflow tube 120 connects between the fluid outlet tube 90 of the vacuum chamber and the upper end 116 of the vacuum inlet 114 on the cylinder 94. The fluid supply tube 118 and the sample fluid overflow tube 120 are preferably formed of clear, flexible plastic so that the user can see the flow of sample fluid therethrough, and detect any blockages which may occur.

The upper part 76 of the vacuum chamber 72 can have a bracket 122 fixed thereto, which fits on a collar 124 on the cylinder 94.

Figure 7:
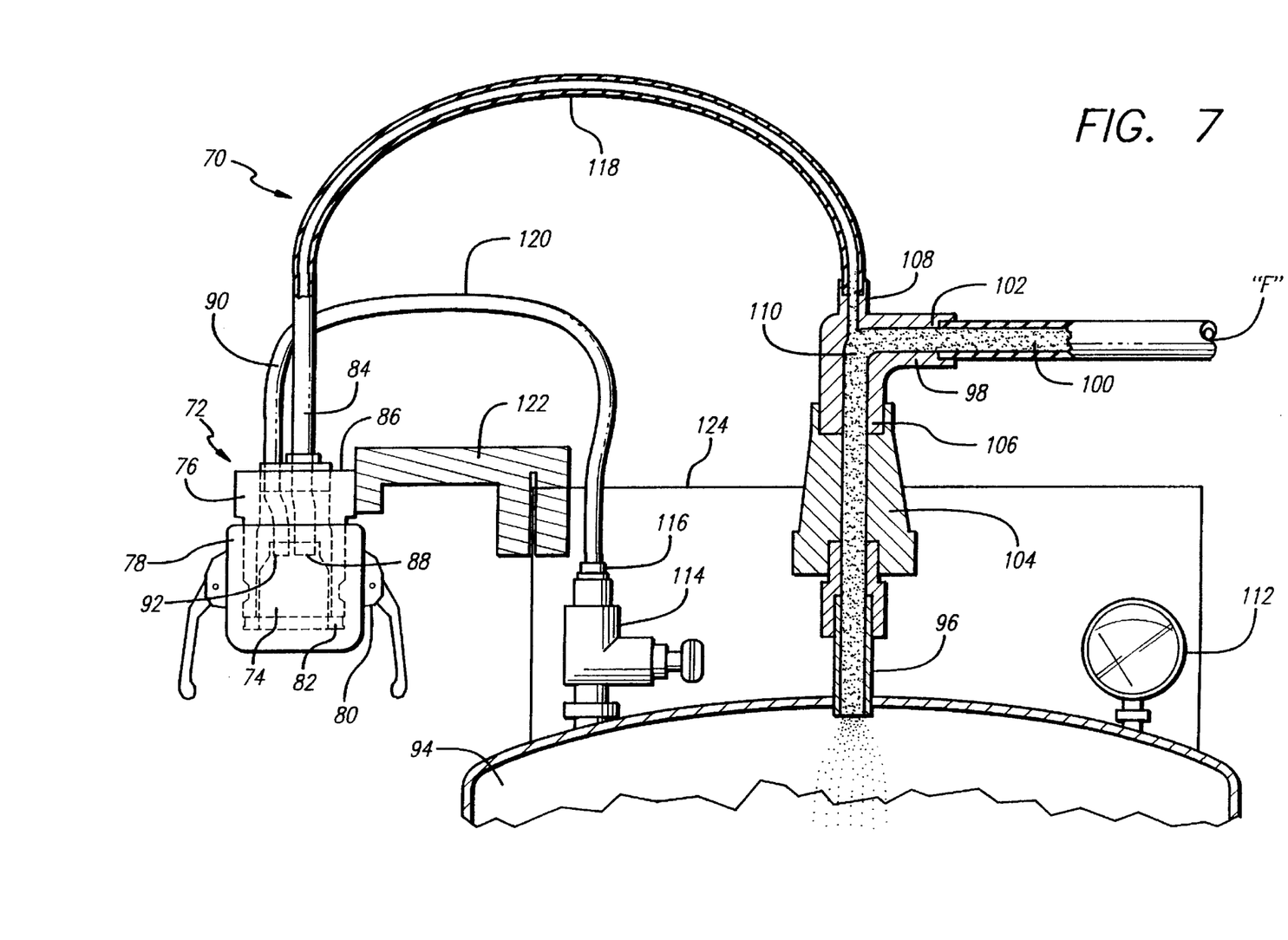
FIG. 7 is an exposed side view of a third embodiment of a fluid sampler of the invention as the fluid sampling is initiated.
Figure 8:
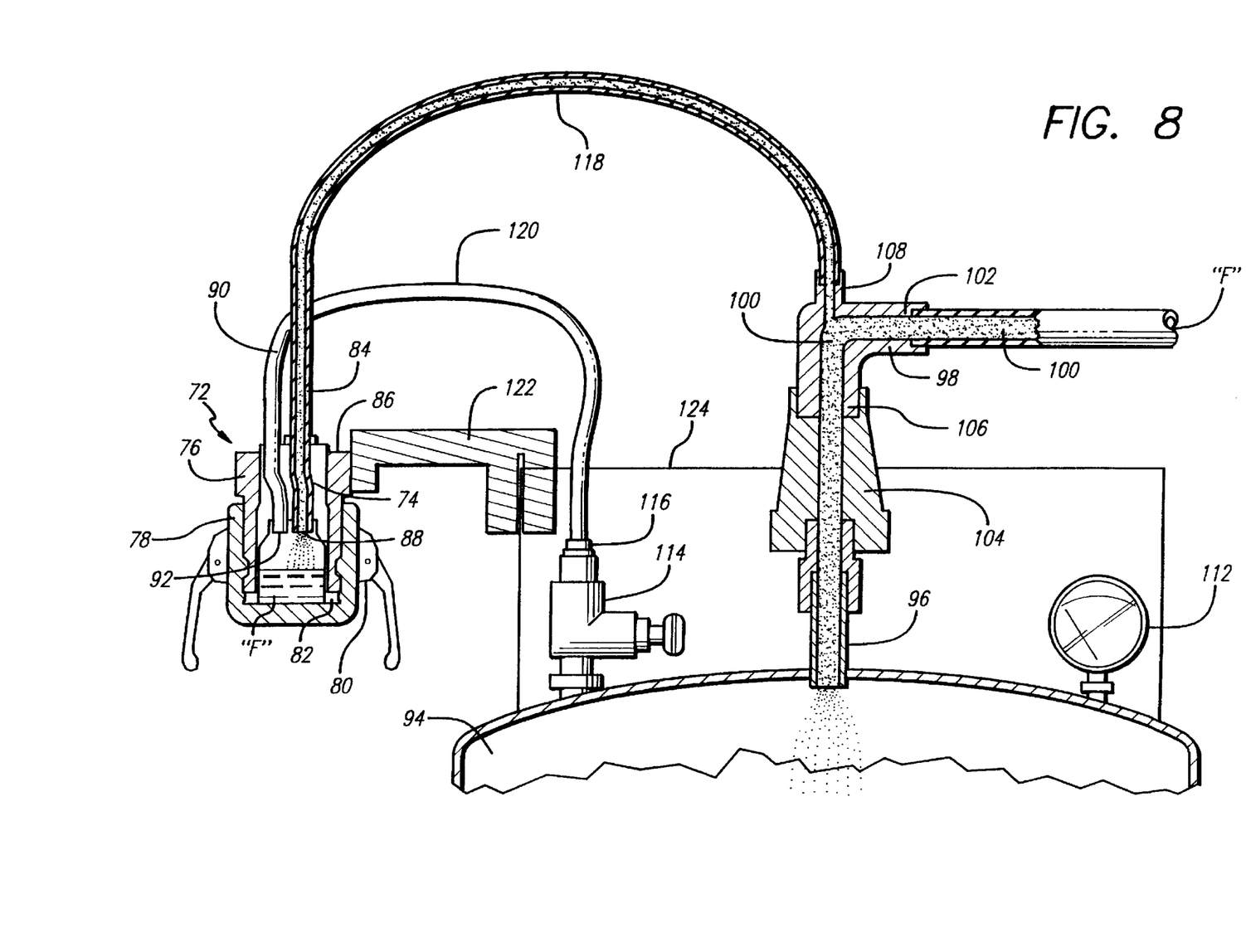
FIG. 8 is an exposed side view of the third embodiment of the device of FIG. 7, with the fluid sample container in the process of being filled.

The operation of the third embodiment of the on-line fluid sampler device 70 is now described with reference to FIGS. 7–10. Referring first to FIG. 7, the two halves 76 and 78 of the fluid chamber 72 are fitted together with the fluid sample container 74 located therein. The open end 88 of the fluid inlet tube 84 and the open end 92 of the fluid outlet tube 90 are positioned in the fluid sample container 74, again with the level of the open end 92 of the fluid outlet tube 90 lower than the level of opening 88 of the fluid inlet tube 84. With the device 70 fitted to the vacuum cylinder 94, a vacuum is established in the cylinder 94. Waste fluid "F" will be drawn through the waste fluid supply tube 100 and into the cylinder 94. However, since a vacuum is also established in the vacuum chamber 72 by virtue of a vacuum being exerted through the sample fluid overflow tube 120 and fluid sample supply tube 118, fluid will also flow up the top port 108, through the fluid sample supply tube 118, and into the fluid sample container 74 in the vacuum chamber 72, as shown in FIG. 8.

Figure 9:
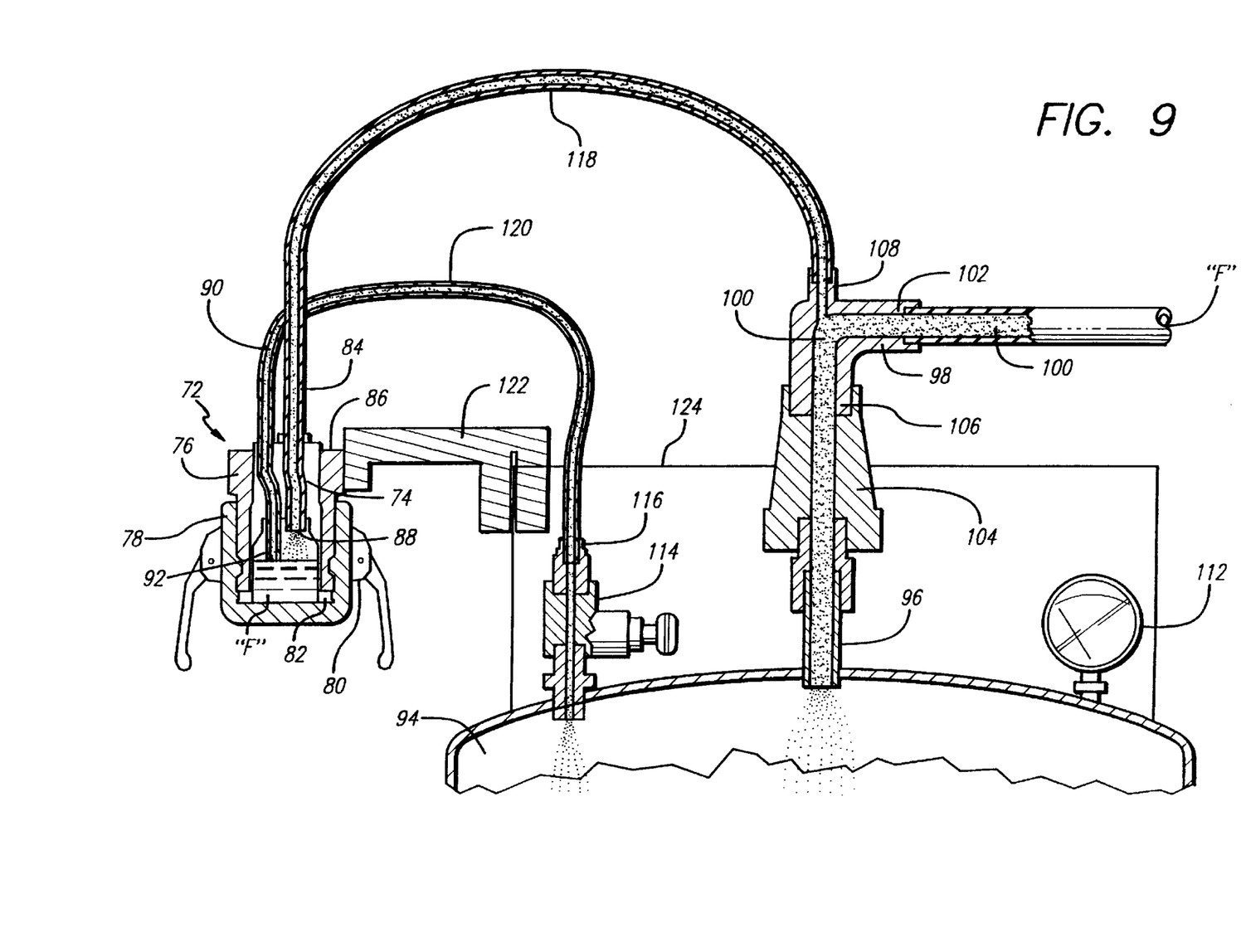
FIG. 9 is an exposed side view of the third embodiment of the device of FIG. 7, with the fluid sample container filled with fluid.

Referring now to FIG. 9, when the level of fluid "F" in the sample container 74 reaches the level of the open end 92, fluid will begin to be suctioned up through the fluid overflow tube 120 and into the cylinder 94. The internal diameter of the fluid overflow tube 120 can be sized to be significantly smaller than the internal diameter of the fluid sample tube 118 since the fluid overflow tube 120 functions mainly to establish a vacuum in the vacuum chamber 72, which can be accomplished with a small interior diameter tube as well as a large interior diameter tube.

For use with taking a sample of used motor oil, as the used motor oil is suctioned through the waste fluid supply tube 100, a sample of the waste oil will fill the sample fluid container 74 to be a predetermined level. After all the waste fluid is drained up through the tube 100 and into the cylinder 94, the vacuum will clear out any waste fluid remaining in the fluid supply tube 118 and overflow tube 120.

Figure 10:
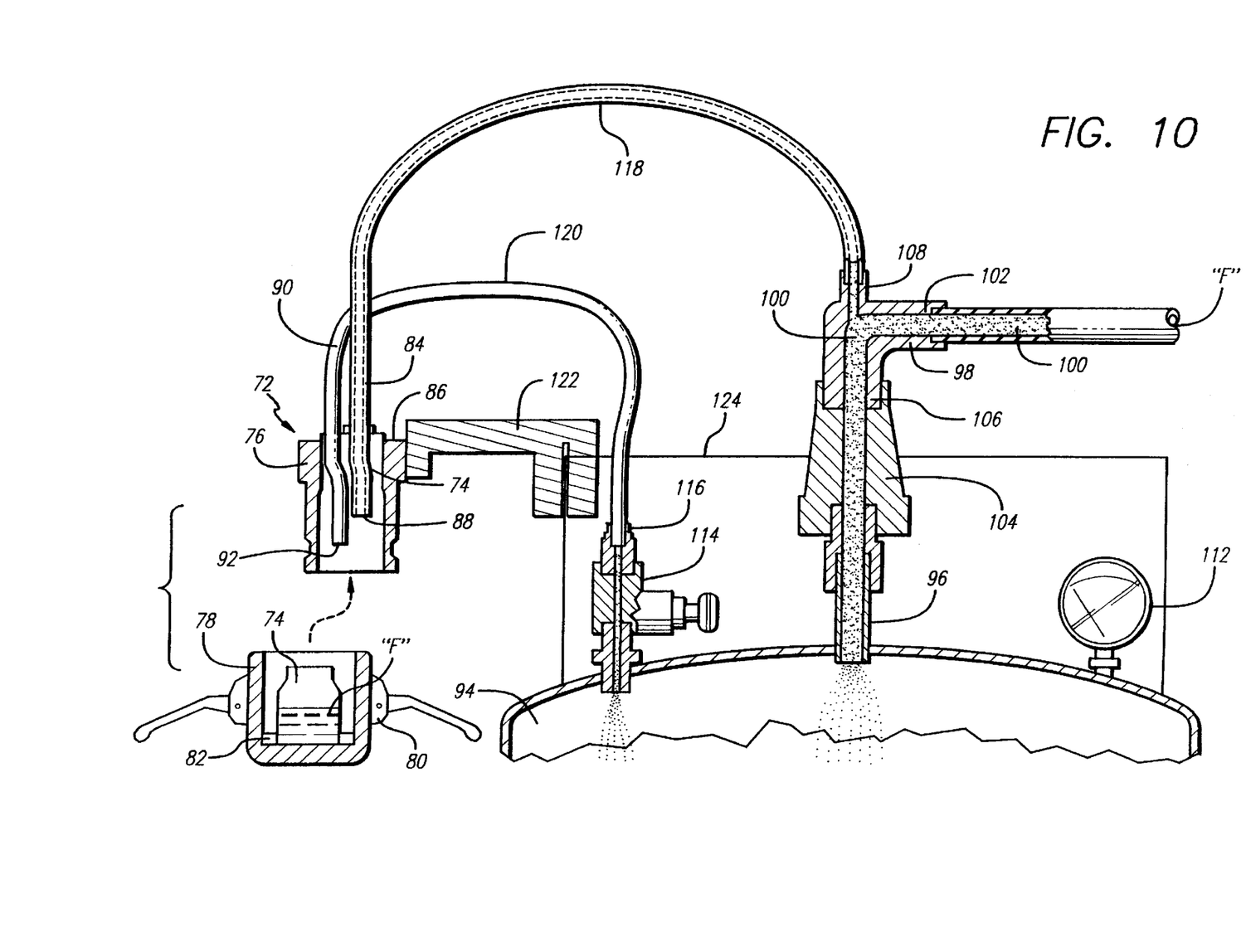
FIG. 10 is an exposed side view after the fluid sample has been taken.

Referring now to FIG. 10, after the used oil is removed from the vehicle, the lower portion 78 of the vacuum chamber is disengaged from the upper portion 76 by deactivating the kamlok 80. The sample fluid filled container 74 can then be removed and sent for analysis of the sample of used oil.

By adjusting the size of the tubes 118 and 120, the rate as which fluid "F" to be samples flows into and out of the sample container 74 can be adjusted. In order to permit the used fluid filled sample container 74 to be removed from the vacuum chamber 72 while waste fluid is still being removed from a waste fluid source, without losing the vacuum in the cylinder 94, quick connect hydraulic fittings or valves can be placed between the vacuum chamber and the fluid supple tube 118 and overflow tube 120 (not shown). Also, while a kamlock 80 is shown as used to provide sealing between the two halves 76 and 78, they can also screw together, or be connected together by other known means.

The drawings and the foregoing description are not intended to represent the only form of the invention in regard to the details of its construction and manner of operation. In fact, it will be evident to one skilled in the art that modifications and variations may be made without departing from the spirit and scope of the invention. Changes in form and in the proportion of parts, as well as the substitution of equivalents, are contemplated as circumstances may suggest or render expedient; and although specific terms have been employed, they are intended in a generic and descriptive sense only and not for the purpose of limitation, the scope of the invention being delineated in the following claims:

I claim:

1. An on-line fluid sampling device, for connection to a vacuum cylinder into which fluid is suctioned into, said device comprising:

a fluid sample container;

a vacuum chamber which is sized to receive the fluid sample container, the vacuum chamber comprising two portions which are detachably attachable together in an airtight manner to permit quick access to the fluid sample container;

a fluid supply tube in connection between a source of fluid to be sampled and said vacuum chamber;

a fluid overflow tube in connection between said vacuum chamber and the vacuum cylinder.

2. The on-line fluid sampling device of claim 1, wherein the two portions of the vacuum chamber are sealably fittable together with a clamp lock fitting.

3. The on-line fluid sampling device of claim 1, wherein said fluid supply tube and said fluid overflow tube comprise clear tubing.

4. The on-line fluid sampling device of claim 1, wherein said device further comprises a T-fitting affixed to said vacuum cylinder to which is connected said fluid supply tube.

5. The on-line fluid sampling device of claim 1, wherein fluid supply tube and said fluid overflow tube have open ends which extend into said vacuum chamber, with said open end of said fluid supply tube being positioned higher relative to said open end of said fluid overflow tube.

\* \* \* \* \*